United States Patent [19]

Bhuvaneshwar et al.

[11] Patent Number: 5,458,826
[45] Date of Patent: Oct. 17, 1995

[54] METHOD OF PRODUCING A HEART VALVE DISC

[75] Inventors: Gobichettipalayam S. Bhuvaneshwar; Muraleedharan C. Vayalappil; Omana A. S. N. Nair, all of Kerala, Ind.

[73] Assignee: Sree Chitratirunal Institute for Medical Sciences and Technology, Kerala, Ind.

[21] Appl. No.: 63,915

[22] Filed: May 17, 1993

[30] Foreign Application Priority Data

Jun. 1, 1992 [IN] Ind. ................... 329/MAS/92

[51] Int. Cl.⁶ ................... B05B 3/00; B06B 3/00
[52] U.S. Cl. ................... 264/442; 264/28; 264/162; 264/235
[58] Field of Search ................... 264/23, 28, 162, 264/235, 346

[56] References Cited

U.S. PATENT DOCUMENTS

| | | | |
|---|---|---|---|
| 4,510,108 | 4/1985 | Cleereman et al. | 264/119 |
| 4,822,355 | 4/1989 | Bhuvaneshwar | 613/2 |
| 5,026,511 | 6/1991 | Sano et al. | 264/28 |
| 5,096,654 | 3/1992 | Craggs et al. | 264/570 |

*Primary Examiner*—Christopher A. Fiorilla
*Attorney, Agent, or Firm*—Helfgott & Karas

[57] ABSTRACT

An improved valve assembly having a valve housing of cobalt-nickel or cobalt-chromium-tungsten based alloy or of titanium/titanium alloys, a sewing ring component of polyester held to the outer surface of the valve housing a disc accruder tiltably held on suitable supports within the housing, the valve disc being made of modified ultra high molecular weight polyethylene. The manufacture of the valve disc and modification of the UHMW-PE takes place simultaneously and comprises cryo machining of a blank of UHMW-PE, solid state compaction, annealing of the compact followed by further cryo machining, annealing and cleaning steps.

9 Claims, 1 Drawing Sheet

METHOD OF PRODUCING A HEART VALVE DISC

This invention relates to improvements in or relating to prosthetic cardiac valve and to the method of manufacturing same.

It is already known to have several types of artificial heart valves all of which generally operate due to the continuous pumping action of the heart. These heart valves usually function as check valves ensuring unidirectional flow of blood.

This invention more particularly relates to improvements in or relating to artificial heart valves which have a plate or disc mounted tiltably in a cage, which cage has an outer ring of a sewing component adapted to be secured inside the heart where required. Bileaflet heart valves are also in vogue of several constructions like single plate heart valves.

Since heart valves are to function continuously and the disc which is tiltably mounted has to flutter more than 115,000 times per day in a normal person having 72 to 80 beats per minute, the artificial disc used has to have long operational life, abrasion and wear resistance and should also maintain the same clearance between it and the valve housing for a long time so that replacement is not necessary. Once installed, the heart valve has to function flawlessly for years and, therefore, it is most important to have proper choice of the materials of the various components and optimize their construction. There are a number of Patents already granted and a considerable amount of/literature is also available on heart valves including the Applicants own earlier U.S. Pat. No. 4,822,355 (Ind. Pats. 159244, 167706). Several other U.S. Patents of relevance that have already been studied by the Applicant include U.S. Pat. No. 4,532,659, U.S. Pat. No. 4,687,487, U.S. Pat. No. 4,263,68, U.S. Pat. No. 2,947,716, U.S. Pat. No. 4,057,857, U.S. Pat. No. 4,494,253, U.S. Pat. No. 4,494,253, U.S. Pat. No. 3,959,827, U.S. Pat. No. 3,824,629, U.S. Pat. No. 3,698,018, U.S. Pat No. 3,737,919, U.S. Pat. No. 3,835,475, U.S. Pat. No. 5,026,391. German Patent DE-A. 3504962 and several other literature references have also been studied.

As already stated there are many types of mechanical heart valve prostheses currently in use, viz. caged ball valves (e.g. Starr-Edwards ball valve), tilting disc valves (e.g. Bjork-Shiley valve, Mealtronic-Hall valve) and bileaflet valves (St. Jude Medical Valve).

The disc of a tilting disc valve has to open and close 40 million times a year at an average, causing tremendous strain on the material. So the material used should be extremely durable in terms of wear resistance and fatigue strength. A valve may have to operate inside the human body up to 25 years or more which necessitates the material to have excellent chemical and structural stability. The biocompatibility (both tissue compatibility and blood compatibility) of the material is also a major requirement to ensure acceptability of the implant by the body. Finally the material should be processable to achieve the required surface finish and dimensional stability.

Towards achieving the above objectives, many researchers have come out with several suggestions both patented and otherwise published.

Thus, although many polymer materials were suggested for use in prosthetic heart valves, only silicon rubber (used in Starr-Edwards ball Valves) has gained acceptability among them. Polyethylenes are another family of materials suggested by other groups. But all forms of Polyethylenes are not suitable for using as disc material in valves.

The intensive study by the Applicant has shown that Low Density Poly Ethylene (LDPE) does not have the required wear resistance and load bearing capacity to be used for this application. High Density polyethylene (HDPE), being more amorphous in nature, exhibits lower toughness, fatigue strength and decreased stress crack resistance.

It is thus a field open for further research and development and the search is still on for a near ideal material.

It has been found by the Applicant that a modified form of Ultra High Molecular Weight Poly Ethylene (UHMW-PE) is best suited for the purposes of heat valve applications.

As such, UHMW-PE is being used in certain orthopedic implants (especially as acetabular cups in total hip joints) and has excellent track record as a load bearing material, in these applications, UHMW-PE exhibits excellent tissue and blood compatibility and is stable (both chemically and structurally) for long duration of working in physiological environments. It has extremely good wear resistance, fatigue strength and toughness.

However, due to the poor melt flow properties of UHMW-PE, it is difficult to prepare heart valve discs/plates out of UHMW-PE, to achieve the desired high degree of surface finish.

It is very important that heart valve discs possess a very high degree of surface finish so that the tendancy of clot formation of the flowing blood on the disc surface is subtantially eliminated. It is required to have a surface finish of the order of 0.1 micron or better.

Due to the high melt flow index, particles of UHMW-PE do not melt and fuse uniformly during conventional compression moulding using resin powder. This produces local regions of poorly fused UHMW-PE which are susceptible to high rates of degradation.

It is, therefore, an object of this invention to propose improved heart valve disc using modified UHMW-PE which will ensure molded heart valve disc which can be given high surface finish and combine all the other advantageous properties such as durability, logevity, high stress resistance, wear resistance, blood compatability, etc.

It is another object of this invention to propose a method for preparing modified UHMW-PE suitable for the manufacture of improved heart valve disc.

It is a further object of this invention to propose a carefully controlled method of manufacturing improved heart valve disc from modified UHMW-PE which method is dependable and reproducible.

In short, the method of preparing the heart valve disc involves a Solid State Compaction technique for generating the required surface finish along with a cryo-machining technique for flash removal.

DETAILED DESCRIPTION OF THE PREFERRED EMBODIMENTS

Figure 1:
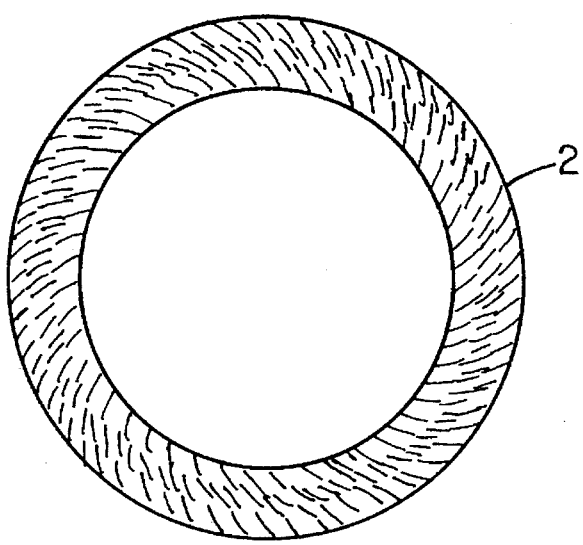
FIG. 1 is plan view of sewing ring 2.
Figure 5:
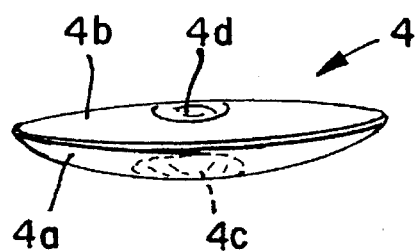
FIG. 5 is a side sectional view of the occluder disc.
Figure 2:
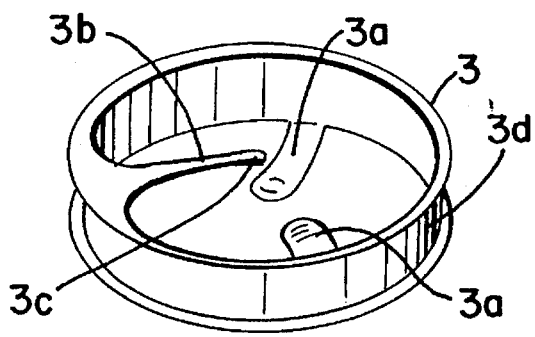
FIG. 2 is a prospective view of the valve housing.
Figure 3:
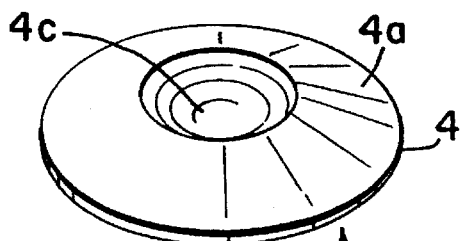
FIG. 3 is a view of the valve occluder disc.
Figure 4:
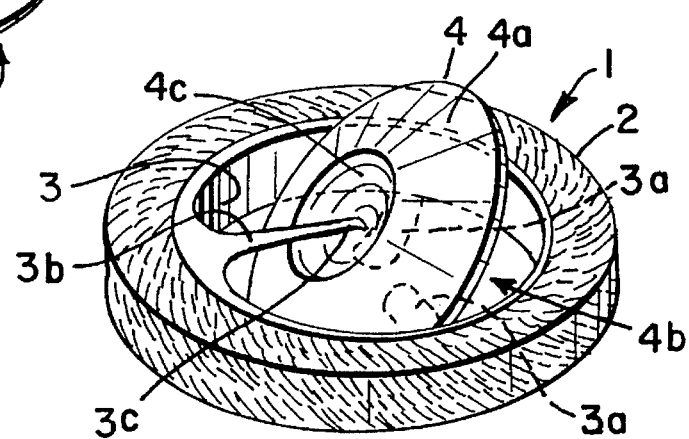
FIG. 4 is a view of the assembled valve structure.

Thus, according to this invention there is provided an improved heart valve assembly comprising sewing ring component 2, metallic valve housing component 3, and a disc occluder 4, said disc occluder being held tiltably on supports within the enclosed space of the valve housing component, said valve housing component having a grooved ring portion externally and having said sewing ring component accommodated on same.

The disc occluder is provided with a substantially flat surface 4b on one side and a substantially tapered surface 4a on the opposite side thereof.

The disc occluder is provided with a centrally depressed portion 4c for engaging it on suitable support means of the valve housing, the depression being provided on the tapered side of the disc occluder.

The disc occluder is optionally provided with a marginally depressed portion 4d on the substantially flat surface, the depressed portion being not as prominent as the depressed portion on the other side of the disc.

The disc occluder is fabricated by injection moulding or machining or grinding or sintering depending on the type of the material.

The disc occluder is polished to a surface finish of 0.1 micron or better using standard polishing techniques.

The valve housing which is circular in shape has a grooved portion 3d externally for accommodating the sewing ring component while the internal side of the housing is plain.

Thus, according to this invention there is provided an improved heart valve assembly comprising a sewing ring component, mounted on the outer circumference of a valve housing component, a disc occluder mounted within the inner circumference of the valve housing, said disc occluder being held tiltably on supports within the enclosed space of the valve housing component, said valve housing component having a grooved ring portion externally on which is mounted said sewing ring component, the sewing ring component being fabricated from polyester, the valve housing being fabricated of a cobalt-nickel based or cobalt-chromium-tungsten based alloy or titanium and its alloys and wherein the valve disc is fabricated from modified UHMW-PE, as herein described. The fabrication of the disc and the modification of the UHMW-PE take place simultaneously.

Further, according to this invention there is provided a method for the preparation of improved heart valve disc from polyethylene which comprises:

(i) subjecting a ram extruded UHMW-PE rod of suitable size to machining under cryo-machining conditions at temperatures below 0° C. to obtain a blank corresponding to the shape of the heart valve disc;

(ii) subjecting the blank obtained in step (i) above to a solid state compaction step at temperatures not exceeding 150° C. and at forces not exceeding 30 KN, in a suitable die, to obtain compacted disc of the required profile and corresponding to the die used;

(iii) annealing the compacted disc in a water bath to relieve the disc of any thermally generated stress in step (ii) above;

(iv) subjecting the annealed disc to a step of edge trimming under cryo-machining conditions to remove any thin flashes produced on the edge of the disc in step (i) above;

(v) followed by a further annealing step in water to relieve from the formed disc any thermal stress produced in step (iv); and (vi) finally subjecting the so formed disc to a step ultrasonic cleaning to remove any surface contamination.

(a) The disc annealing is done for a suitable duration between 1 to 6 hrs at a temperature below 123° C.

(b) The cooling rate is less than 1° C. per minute.

The ram extruded UHMW-PE rod is subjected to cryo-machining at temperatures below 0° C.

The cryo-machining is carried out in the presence of anti-freeze and anti-rust coolant.

The anti-freeze and anti-rust coolant is a mixture or polypropylene glycol and water. Though a range of ratios of these two liquids can be used, it is advantageous to use a mixture having polypropylene glycol and water in the ratio of 1:1.5 by volume.

For optimum results and to prevent corrosion, the coolant also includes inorganic salts such as potassium dichromate, sodium nitrate, sodium bicarbonate and borax in suitable weight percentages/ratios so that the pH of the medium is around 8.5. The pH can vary slightly either way.

We claim:

1. A method for the preparation of an improved heart valve disc from polyethylene which comprises;

(i) subjecting a ram extruded WHMW-PE rod to machining under cryo-machining conditions at a temperature below 0° C. to obtain a blank corresponding to a shape of the heart valve disc;

(ii) subjecting the blank obtained in step (i) to a solid state compaction step at a temperature not exceeding 150° C. and at forces not exceeding 30 KN, in a die, to obtain a compacted disc and corresponding to the die;

(iii) annealing the compacted disc in a water bath to relieve the disc of any stress thermally generated in step (ii);

(iv) subjecting the annealed disc to edge trimming under cryo-machining conditions to remove any thin flashes produced on an edge of the disc in step (i);

(v) further annealing the annealed disc in water to relieve from the disc any thermal stress produced in step (iv); and (vi) finally subjecting the disc to ultrasonic cleaning to remove any surface contamination.

2. A method as claimed in claim 1 wherein the disc annealing is done for a duration between 1 to 6 hrs at a temperature below 120° C.

3. A method as claimed in claim 2 wherein cooling of the annealed disc is carried out by cooling at a rate of less than 1° per minute.

4. A method as claimed in claim 1 wherein the ram extruded UHMW-PE rod is subjected to cryo-machining at temperatures below 0° C.

5. A method as claimed in claims 1 and 4, wherein the cryo-machining for step (i) is carried out in the presence of anti-freeze and anti-rust coolant.

6. A method as claimed in claim 5 wherein the anti-freeze and anti-rust coolant is a mixture of polypropylene glycol and water.

7. A method as claimed in claim 6 wherein said mixture has polypropylene glycol and water in the ratio of 1:1.5 by volume.

8. A method as claimed in claim 5 wherein said coolant also includes inorganic salts selected from the group consisting of potassium di-chromate, sodium nitrate, sodium bicarbonate and borax so that the pH is about 8.5.

9. A method as claimed in claim 4, wherein the cryo-machining for step (i) is carried out in the presence of anti-freeze and anti-rust coolant.

* * * * *